US006930130B2

(12) United States Patent
Hopmann et al.

(10) Patent No.: US 6,930,130 B2
(45) Date of Patent: Aug. 16, 2005

(54) CITRULLIMYCINES, A PROCESS FOR THEIR PRODUCTION AND THEIR USE AS PHARMACEUTICALS

(75) Inventors: Cordula Hopmann, Frankfurt am Main (DE); Michael Kurz, Hofheim (DE); Mark Brönstrup, Frankfurt (DE); Joachim Wink, Rödermark (DE)

(73) Assignee: Aventis Pharma Deutschland GmbH, Frankfurt am Main (DE)

( * ) Notice: Subject to any disclaimer, the term of this patent is extended or adjusted under 35 U.S.C. 154(b) by 0 days.

(21) Appl. No.: 09/966,109

(22) Filed: Oct. 1, 2001

(65) Prior Publication Data

US 2002/0065316 A1 May 30, 2002

(30) Foreign Application Priority Data

Oct. 2, 2000 (EP) .............................................. 00121566

(51) Int. Cl.$^7$ ..................... A61K 31/13; C12N 1/00; C07D 211/70
(52) U.S. Cl. ..................... 514/579; 435/132; 435/886; 546/313
(58) Field of Search .................. 546/313; 435/886, 435/132; 514/579; 560/313

(56) References Cited

U.S. PATENT DOCUMENTS 5,252,472 A * 10/1993 Grabley et al. ............. 435/126

OTHER PUBLICATIONS

March, J., Advanced Organic Synthesis, 4$^{th}$ Edition, pp. 393–396, 1213 (1992).
Remington's Pharmaceuticals Sciences, 17$^{th}$ Edition, Mack Publishing Co., (Alfonso R. Gennaro, editor), pp. 1418–1419 (1989)..

* cited by examiner

Primary Examiner—Elli Peselev
(74) Attorney, Agent, or Firm—Finnegan, Henderson, Farabow, Garrett & Dunner, L.L.P.

(57) ABSTRACT

The present invention relates to novel active compounds named Citrullimycines, which are obtainable by cultivation of *Streptomyces* sp. ST 101396 (DSM 13309), and to their pharmaceutically acceptable salts and derivatives. The present invention further relates to a process for the production of the Citrullimycines, to the microorganism *Streptomycetes* sp. ST 101396 (DSM 13309), to the use of the Citrullimycines and their pharmaceutically acceptable salts and derivatives as pharmaceuticals, for example as inhibitors of the neurotensin receptor, and to pharmaceutical compositions comprising Citrullimycines or a pharmaceutically acceptable salt or derivative thereof.

21 Claims, No Drawings

CITRULLIMYCINES, A PROCESS FOR THEIR PRODUCTION AND THEIR USE AS PHARMACEUTICALS

The present invention relates to novel active compounds called Citrullimycines, which are obtainable by cultivation of *Streptomycetes* sp. ST 101396 (DSM 13309), and to their pharmaceutically acceptable salts and derivatives. The present invention further relates to the *Streptomycetes* sp. ST 101396 (DSM 13309), to a process for the production of Citrullimycines, to the use of the Citrullimycines as pharmaceuticals, for example their use as substances with an affinity for neurotensin receptors, and to Citrullimycine-containing pharmaceuticals.

Neurotensin is a brain and gastrointestinal 13-amino acid hormonal peptide, which is involved in the control of a broad variety of physiological activities as a central neurotransmitter or neuromodulator in both the central nervous system and in the periphery. Neurotensin fulfills many functions through interaction with specific receptors, which have been characterized in several tissues and cell lines of peripheral and central organs. Some studies have suggested the involvement of neurotensin in schizophrenia, Parkinson's disease, and Alzheimer's disease. Therefore, compounds with an affinity for neurotensin receptors are expected to be useful in the treatment of these diseases.

It has now been found that the microorganism *Streptomycetes* sp. ST101396, (DSM 13309), is able to form novel active substances that inhibit the human neurotensin receptor proteins expressed in Human Embryonic Kidney (HEK) cell membranes.

Other than in the operating examples, or where otherwise indicated, all numbers expressing quantities of ingredients, reaction conditions, and so forth used in the specification and claims are to be understood as being modified in all instances by the term "about." Accordingly, unless indicated to the contrary, the numerical parameters set forth in the following specification and attached claims are approximations that may vary depending upon the desired properties sought to be obtained by the present invention. At the very least, and not as an attempt to limit the application of the doctrine of equivalents to the scope of the claims, each numerical parameter should be construed in light of the number of reported significant digits and by applying ordinary rounding techniques.

Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard deviation found in their respective testing measurements.

One embodiment of the present invention relates to Citrullimycines, which are active substances obtainable from the strain *Streptomycetes* sp. DSM 13309, and to their physiologically tolerated salts, esters, ethers and other chemical equivalents.

Accordingly, in one embodiment, the present invention relates to compounds of the formula (I) below and their physiologically tolerated salts and derivatives, such as, for example, esters, ethers and other chemical equivalents, including all stereoisomeric forms and all tautomeric forms.

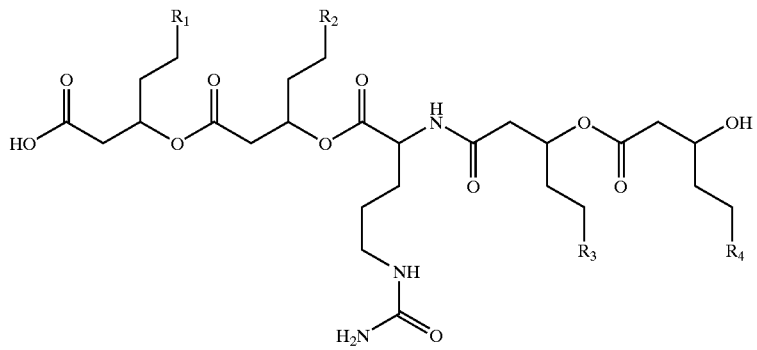

(I)

where:

$R_1$, $R_2$, $R_3$, and $R_4$ are, independently of one another, alkyl residues with 1 to 6 carbon atoms.

The alkyl residues in the compounds of the formula (I) can be straight-chain or branched.

Examples of alkyl residues include, but are not limited to, methyl, ethyl, propyl, butyl, pentyl, hexyl, isopropyl, isobutyl, isopentyl, sec-butyl, tertbutyl, or neopentyl.

Other embodiments of the invention include:

1) Compounds of the formula (I) above in which one of the residues $R_1$, $R_2$, $R_3$, or $R_4$ is a straight or branched propyl residue and the rest of the residues are straight or branched butyl residues (Citrullimycine A: molecular formula: $C_{41}H_{75}N_3O_{11}$, MW: 785) and their physiologically tolerated salts and derivatives thereof;

2) Compounds of the formula (I) above in which either:

(a) two of the residues $R_1$, $R_2$, $R_3$, or $R_4$ are straight or branched butyl residues and two of the residues are straight or branched propyl residues; or (b) $R_1$, $R_2$, $R_3$, and $R_4$ are one butyl, one pentyl, one ethyl and one propyl residue, in any order, the residues being either straight chain or branched (Citrullimycine B: molecular formula: $C_{40}H_{73}N_3O_{11}$, MW 771) and their physiologically tolerated salts and derivatives thereof; and 3) Compounds of the formula (I) above in which either:

(a) $R_1$, $R_2$, $R_3$, and $R_4$ are straight or branched butyl residues; or (b) two of the residues $R_1$, $R_2$, $R_3$, and $R_4$ are straight or branched butyl residues, one is a straight or branched propyl residue and one is a straight or branched pentyl residue (Citrullimycine C: molecular formula: $C_{42}H_{77}N_3O_{11}$, MW 799) and their physiologically tolerated salts and derivatives thereof.

It is understood that the compounds of formula (I) may exist in a variety of isomeric configurations, including structural isomers, tautomers, and stereoisomers. It is further understood that the present invention encompasses compounds of formula (I) in each of their various structural and stereoisomeric configurations, as individual isomers and as mixtures of isomers.

The Citrullimycines A to C are typically isolated as a mixture of isomers. With respect to Citrullimycine A, for example, an isolated sample may comprise a mixture of two or more of the following isomers:

Isomer 1: R1, R2, and R4=—CH(CH3)CH2CH3, R3=—CH(CH3)CH3

Isomer 2: R1, R2, and R3=—CH(CH3)CH2CH3, R4=—CH(CH3)CH3

Isomer 3: R1, R3, and R4=—CH(CH3)CH2CH3, R2=—CH(CH3)CH3

Isomer 4: $R_1$=—$CH(CH_3)CH_3$, $R_2$, $R_3$, and $R_4$=—$CH(CH_3)CH_2CH_3$

The isomers of Citrullimycine A may exist in any ratio in the mixture isolated.

Citrullimycines A–C may be characterized by any one or more of their physico-chemical and spectral properties, such as their mass spectrometry, 1H NMR, or 13C NMR spectroscopic data (see Tables 1 and 2 below).

The compounds of the formula (I) may be described as a sequence of four β-hydroxyacids with a citrulline molecule incorporated in the middle of the sequence. Citrullimycines A–C differ in the length of the alkylchain of the β-hydroxyacids.

The compounds of the formula (I) are obtainable by cultivation of the microorganism Streptomycetes sp. ST 101396, (DSM 13309). This microorganism was deposited on Feb. 14, 2000, with the German Collection of Microorganisms and Cell Cultures (DSMZ-Deutsche Sammlung von Mikroorganismen und Zellkulturen GmbH), Braunschweig, Germany and has been given the accession number DSM 13309.

Another embodiment of the present invention is directed to a process for the production of compounds of the formula (I), which comprises cultivating the microorganism Streptomycetes species DSM 13309, or one of its mutants or variants, under aerobic conditions in a nutrient medium containing one or more sources of carbon and one or more sources of nitrogen and, optionally, nutrient inorganic salts and/or trace elements, and then isolating and purifying the compounds of the formula (I) in a customary manner.

Mutants and variants of the microorganism DSM 13309 may also be able to synthesize Citrullimycines according to the present invention. A mutant in this context refers to a microorganism in which at least one gene has been modified. This modification, however, does not affect the ability of the microorganism to produce the compounds of formula (I). Such mutants may be produced by methods known in the art, for example, by irradiation such as with ultraviolet- or X-rays, or by treatment with chemical mutagens, such as, for example, ethylmethylansulfonate (EMS), 2-hydroxy-4-methoxy-benzophenone (MOB), or N-methyl-N'-nitro-N-nitrosoguanidine (MNNG), or as described by Brock et al. in "Biology of Microorganisms" Prentice Hall, pages 238–247 (1984). A variant refers to a phenotype of a microorganism. Microorganisms have the ability to adapt to environmental changes. This adaptive capacity is the reason for the observed physiological flexibility in nature. In phenotypic adaptation, all cells of a population are involved. This type of change is not genetically conditioned, but it is a modification that under altered conditions is reversible (H. Stolp, "Microbial Ecology: organisms, habitats, activities" Cambridge University Press, Cambridge, G.B., page 180 (1988)).

The screening for suitable mutants and variants that can produce the compounds according to the invention can be confirmed by determination of the biological activity of the active compounds accumulated in the culture broth, for example by testing for neurotensin inhibitory action following the protocols of Examples 3 and 4, or by detecting in the culture broth compounds that are known to be active by, for example, HPLC or LC-MS methods.

The nutrient medium may contain sources of carbon, nitrogen and nutrient inorganic salts. The carbon sources may include, for example, starch, glucose, sucrose, dextrin, fructose, molasses, glycerol, lactose, galactose, or combinations thereof. The sources of nitrogen may include, for example, soybean meal, peanut meal, yeast extract, beef extract, peptone, malt extract, corn steep liquor, gelatin, casamion acids, or combinations thereof. The nutrient inorganic salts may include, for example, sodium hydrogen phosphate, potassium hydrogen phosphate, ammonium hydrogen phosphate, sodium chloride, calcium chloride, calcium carbonate, potassium nitrate, ammonium sulphate, magnesium sulphate, cobalt(II) chloride, or combinations thereof.

The cultivation of strain DSM 13309, or one of its variants and mutants, may be carried out at temperatures in the range from about 20° C. to about 35° C. and a pH in the range from about 5.0 to about 8.0, for example, at about 27° C. and a pH in the range from about 6.8 to about 7.0.

The cultivation of strain DSM 13309, or one of its variants and mutants, may be carried out for about 48 hr to about 240 hr, when an optimal yield of the Citrullimycines of the invention may be obtained. The cultivation may be carried out, for example, by fermentation for about 60 hr to about 120 hr under submerged conditions, for example in shake flasks or in laboratory fermenters. The progress of fermentation and formation of the Citrullimycines can be detected by High Pressure Liquid Chromatography (HPLC) or LC-MS, or by measuring the bioactivity of the culture broth. In the resulting culture broth, the Citrullimycines are present in the culture filtrate as well as in the mycelium. Citrullimycines can be isolated using known separation techniques. For example, Citrullimycines can be recovered from the culture filtrate by extraction with a water-immiscible solvent such as ethyl acetate, dichloromethane, chloroform, or butanol, at a pH in the range from about 3 to about 8 or by hydrophobic interaction chromatography using polymeric resins such as "Diaion HP-20®" or "MCI® Gel CHP-20P" (Mtheirubishi Chemical Industries Limited, Japan), "Amberlite XAD®" (Rohm and Hass Industries U.S.A.), activated charcoal or ion exchange chromatography at a pH in the range from about 3 to about 8. The active material can also be recovered from the mycelium by extraction with a water-miscible solvent such as methanol, acetone, acetonitrile, n-propanol, or iso-propanol or a water-immiscible solvent such as ethyl acetate, dichloromethane, chloroform, or butanol, at a pH in the range from about 3 to about 8. Concentration and lyophilization of the extracts gives the active crude material.

The Citrullimycines of the present invention may, for example, be recovered from the crude material as follows:

By fractionation, using, for example, any of the following techniques: normal phase chromatography (using, for example, alumina or silica gel as stationary phases and eluents such as petroleum ether, ethyl acetate, methylene chloride, acetone, chloroform, methanol, or combinations thereof and addition of amines such as $NEt_3$); reverse phase chromatography (using reverse phase silica gel such as dimethyloctadecylsilylsilica gel, also called RP-18, or dimethyloctylsilyl silica gel, also called RP-8, as stationary phases and eluents such as water, buffers viz. phosphate, acetate, citrate (pH 2–8) and organic solvents such as methanol, acetonitrile, acetone, tetrahydrofuran or combinations of these solvents) gel permeation chromatography using resins such as ®Sephadex LH-20 (Pharmacia Chemical Industries, Sweden), TSKgel ®Toyopearl HW (TosoHaas, Tosoh Corporation, Japan) in solvents such as methanol, chloroform, acetone, ethyl acetate, or their combinations, or ®Sephadex G-10 and G-25 in water; or by counter-current chromatography using a biphasic eluent system made up of two or more solvents such as water, methanol, ethanol, iso-propanol, n-propanol, tetrahydrofuran, acetone, acetonitrile, methylene chloride, chloroform, ethyl acetate, petroleum ether, benzene, or toluene. These and other suitable techniques known in the art may be used repeatedly and/or in combination with one another.

Chemical equivalents ('derivatives') of the compounds according to the invention include compounds derived from a compound of the formula (I) that retain the activity displayed by the compounds of the invention. Said equivalents include, for example, esters, ethers, complexes, or adducts.

The compounds according to the present invention may be converted into pharmaceutically acceptable salts and derivatives, which are all covered by the present invention. The salts and derivatives can be prepared by standard procedures known to one skilled in the art.

Physiologically tolerated salts of the compounds of the formula (i) include both the organic and the inorganic salts thereof as described in Remington's Pharmaceutical Sciences (17th edition, page 1418 (1985)). Salts such as sodium and potassium salts, for example, may be prepared by treating the compounds according to the invention with suitable sodium or potassium bases.

Esters of the free carboxylic acid may be prepared by methods given in the literature, for example, by treatment with an alcohol in the presence of a dehydrating agent like decyclohexylcarbodiimide (DCC), as described in Advanced Organic Synthesis, 4th Edition, J. March, John Wiley & Sons, page 395 (1992).

The ester groups of the compounds according to the present invention may be reduced to ether groups as described in the literature, for example, by treatment with $BF_3$-etherat, $LiAlH_4$, $LiBH_4$, or $NaBH_4$, as described in Advanced Organic Synthesis, $4^{th}$ Edition, J. March, Wiley & Sons, page 1213 (1992). The amide group may be reduced in the same way by reaction with $LiAlH_4$.

The Citrullimycines according to the invention show inhibition in the neurotensin receptor binding assay of human neurotensin receptor proteins expressed in HEK cell membranes. In this assay, Citrullimycine A showed an IC50 of 16 $\mu$M.

The compounds according to the present invention and their pharmaceutically acceptable salts and derivatives can be administered to animals, including mammals and humans, as pharmaceuticals, individually or in mixtures with one another, or in the form of pharmaceutical compositions that permit parenteral administration. Accordingly, one embodiment of the present invention relates to compounds of the formula (I) above and their pharmaceutically acceptable salts and derivatives for use as pharmaceuticals, for example for their use as neurotensin antagonists with an affinity for a neurotensin receptor. Another embodiment of the present invention relates to pharmaceutical compositions that contain an effective amount of one or more of the target compounds and/or one or more pharmaceutically acceptable salts and/or derivatives thereof, together with a pharmaceutically acceptable carrier.

The compounds according to the invention can be administered orally, intramuscularly, intravenously or by other suitable modes of administration known in the art. Pharmaceutical compositions containing these compounds or a pharmaceutically acceptable salt or derivative thereof, optionally with other pharmaceutically active substances, can be prepared by mixing the active compounds with one or more pharmacologically tolerated auxiliaries and/or excipients. The mixture can then be converted into a suitable pharmaceutical form such as tablets, coated tablets, capsules, granules, powders, emulsions, suspensions or solutions.

Examples of auxiliaries and/or excipients include fillers, emulsifiers, lubricants, masking flavours, colorants, buffer substances, tragacanth, lactose, talc, agar-agar, polyglycols, ethanol, and water. Suitable forms for parenteral administration include suspensions or solutions in water. It is also possible to administer the active substances as such, without vehicles or diluents, in a suitable form, for example, in capsules.

Another embodiment of the invention relates to a method for the production of a pharmaceutical, which comprises mixing at least one of the compounds according to the invention with a pharmaceutically suitable and physiologically tolerated carrier and, where appropriate, further suitable active substances, additives or excipients and converting the mixture into a suitable dosage form.

As is customary, the galenic formulation, the method of administration, and the dosage range that are suitable in a specific case depend on the species to be treated and on the state of the respective condition or disease, and can be optimized using methods known in the art.

The following are illustrative examples of the present invention but are not to be considered limitative of the scope thereof.

EXAMPLE 1

Maintenance of the Producer Strain *Streptomycetes* Species ST 101396, DSM 13309

| Composition of maintenance medium | |
| --- | --- |
| The producer strain DSM 13309 was maintained on the following medium: | |
| Malt extract | 10.0 g |
| Glucose | 4.0 g |
| Yeast extract | 4.0 g |
| Agar powder | 15.0 g |
| Demineralised water | 1 liter |
| pH | 7.0–7.5 |

After dissolving the ingredients thoroughly by heating, the resultant solution was distributed in test tubes and sterilized at 121° C. for 20 min. The test tubes were cooled and allowed to solidify in a slanting position. The agar slants were streaked with the *Streptomycetes* sp. ST 101 396, DSM 13309, using a wire loop and incubated at 28° C. (±1° C.) until sufficient growth was observed. These cultures were stored in the refrigerator at +8° C.

| Preparation of glycerol working seed | |
|---|---|
| Composition of medium | |
| Yeast extract | 4 g |
| Soluble starch | 15 g |
| K$_2$HPO$_4$ | 1 g |
| MgSO$_4$ × 7 H$_2$O | 0.5 g |
| Demineralised water | 1 litre |
| pH | 7.0 |

The above medium was distributed in 100-ml aliquots in 300-ml Erlenmeyer flasks and autoclaved at 121° C. for 20 minutes. The flasks were cooled to room temperature and inoculated with the above mentioned agar slant. The incubation was carried out for five days on a rotary shaker at 180 rpm and 28° C. 1.5 ml of this culture were mixed with 1.5 ml glycerol (99%) and stored at −20° C.

EXAMPLE 2

| Fermentation of the strain Strepotomycetes sp. ST 101396, DSM 13309, in shaker flasks | |
|---|---|
| Composition of seed medium: | |
| Glucose | 20 g |
| Soybean meal | 10 g |
| CaCO3 | 0.02 g |
| CoCl2 × 6 H2O | 0.001 g |
| Demineralised water | 1 litre |
| pH | 6.8–7.0 |

The above medium was distributed in 100-ml aliquots in 500-ml Erlenmeyer flasks and autoclaved for 20 min. The flasks were cooled to room temperature and each flask was inoculated with a loopful from one of the above mentioned cultures of Example 1 and shaken on a rotary shaker for 72 hours, at 240 rpm, and at 27° C. (±1° C.) to give seed culture.

| Composition of production medium: | |
|---|---|
| Glucose | 20 g |
| Soybean meal | 10 g |
| CaCO3 | 0.02 g |
| CoCl2 × 6 H2O | 0.001 g |
| Demineralised water | 1 litre |
| pH | 6.8–7.0 |

The production medium was distributed in 100-ml aliquots in 500-ml Erlenmeyer flasks and autoclaved at 121° C. for 20 min. The flasks were cooled to room temperature and inoculated with the above mentioned seed culture (2% v/v). The fermentation was carried out on a rotary shaker at 240 rpm and 27° C. (±1° C.) for 72 hours. The production of the inhibitors Citrullimycine A–C was determined by testing their bioactivity.

EXAMPLE 3

Isolation and Purification of the Citrullimycines A–C

The culture broth (3 liters) was harvested and freeze-dried. The lyophilization product was extracted with methanol (3 liters) and the active extracts were pooled and concentrated under reduced pressure. The product was subsequently freeze-dried to yield 25 g of crude material. This crude material was purified by preparative HPLC using the following conditions:

1.)

| Column: MCI ® Gel CHP-20P (600 × 40 mm; Kronlab) | | | |
|---|---|---|---|
| Eluent: | A) H$_2$O | | B) MeOH |
| Gradient: | min | % A | % B |
| | 0 | 100 | 0 |
| | 17.5 | 100 | 0 |
| | 17.6 | 80 | 20 |
| | 40 | 80 | 20 |
| | 40.1 | 50 | 50 |
| | 55 | 50 | 50 |
| | 55.1 | 30 | 70 |
| | 67.5 | 30 | 70 |
| | 67.6 | 15 | 85 |
| | 72.5 | 15 | 85 |
| | 72.6 | 10 | 90 |
| | 77.5 | 10 | 90 |
| | 77.6 | 0 | 100 |

Flow: 20 ml/min

Detection: 358 nm

The active fractions eluted after 75 min. The pooled fractions were concentrated under reduced pressure and freeze-dried.

Final purification was carried out by preparative HPLC using the following conditions.

1.) Column: Nucleosil 100-RP 18-AB (5μ, 250×21 mm, Macherey & Nagel)

| Eluent: | A) H$_2$O | | B) CH$_3$CN |
|---|---|---|---|
| Gradient: | min | % A | % B |
| | 0 | 70 | 30 |
| | 22 | 70 | 30 |
| | 38 | 52 | 48 |
| | 44 | 52 | 48 |
| | 92 | 0 | 100 |
| | 110 | 0 | 100 |

Flow Rate: 10 ml/min
Detection: 360 nm

The active fractions were analyzed by LC-MS. The Citrullimycine-containing fractions eluted after 87 min (Citrullimycine A), 97 min (Citrullimycine B) and 98 min (Citrullimycine C). The pooled fractions were concentrated under reduced pressure and freeze-dried. The overall yield from a 3-L culture broth was 1 mg of each substance.

The physico-chemical and spectral properties of Citrullimycine A–C are given in Tables 1 and 2.

TABLE 1

| | |
|---|---|
| Appearance | colorless solids |
| Solubility | Methanol, DMSO |
| LC-MS (Liquid Chromatography Mass Spectrometry) | Column: Purospher STAR RP.18e (Merck, 30 × 2 mm, 3 μm) |
| | Eluent: $CH_3CN$/10 mM $NH_4Ac$ (pH 4.5) |

| Gradient: | time | % $CH_3CN$ |
|---|---|---|
| | 0.00 | 5.0 |
| | 6.00 | 100.0 |
| | 6.50 | 100.0 |
| | 7.50 | 5.0 |
| | 8.00 | 5.0 |
| | 9.00 | 100.0 |
| | 9.50 | 100.0 |
| | 10.50 | 5.0 |
| | 13.00 | 5.0 |

Flow: 0.25 ml/min
Temp.: 40° C.
Detection: 210 nm, 230, 250, 320, 400 (UV);
100–2000 amu (MS)

| Citrullimycine A: | |
|---|---|
| Retention time: | 7.3 min |
| ESI-MS (Electrospray Ionisation Mass Spectrometry): | 784.7 amu $(M-H)^-$ |
| HR-FAB-MS (High Resolution: Fast Atom Bombardment MS) | 786.546536 [Calcd for $C_{41}H_{76}N_3O_{11}$: 786.547986 $(M + H)^+$] |
| Molecular formula: | $C_{41}H_{75}N_3O_{11}$ |
| $MS^n$-Experiments: Syringe infusion of sample at 5 μL/min | Instrument: Finngan LCQ |

$ESI^+$:

$MS^2$: 786 amu $(M+H^+)$ gave 769 amu ($-NH_3$), $MS^3$: 769 amu gave 751 amu ($-H_2O$)

$ESI^-$:

$MS^2$: 784 amu $(M-H)^-$ gave 624 amu ($-C_8H_{16}O_3$), 610 amu ($-C_9H_{18}O_3$), 468 amu ($-C_{17}H_{32}O_5$), and 454 amu ($-C_{18}H_{34}O_5$), The products at 624 amu and 610 amu are formed in a 25 to 75 ratio.

$MS^3$: 624 amu gave 468 amu ($-C_9H_{16}O_2$)

$MS^3$: 610 amu gave 468 amu ($-C_8H_{14}O_2$), and 454 amu ($-C_9H_{16}O_2$).

The products are formed in a 33 to 66 ratio.

$MS^3$: 468 amu gave 425 amu ($-HNCO$), 330 amu ($-C_9H_{14}O$), 312 amu ($-1C_9H_{16}O_2$), and 269 amu ($-C_{10}H_{17}NO_3$)

$MS^4$: 425 amu gave 287 amu ($-C_9H_{14}O$), and 269 amu ($-C_9H_{16}O_2$)

$MS^4$: 312 amu gave 269 amu ($-HNCO$)

$MS^5$: 269 amu gave 225 amu ($-CO_2$), and 131 amu ($-C_9H_{14}O$)

$MS^3$: 454 amu gave 411 amu ($-HNCO$), 330 amu ($-C_8H_{12}O$), 316 amu ($-C_9H_{14}O$), 312 amu ($C_8H_{14}O_2$), and 298 amu ($-C_9H_{16}O_2$)

$MS^4$: 411 amu gave 287 amu ($-C_8H_{12}O$), 273 amu ($-C_9H_{14}O$), 269 amu ($-C_8H_{14}O_2$), and 255 amu ($-C_9H_{16}O_2$)

Only nominal masses are given. All given formulas for neutral losses are based on interpretation and are not verified with HR-MS.

$^1H$ NMR: see Table 2

$^{13}C$ NMR: see Table 2

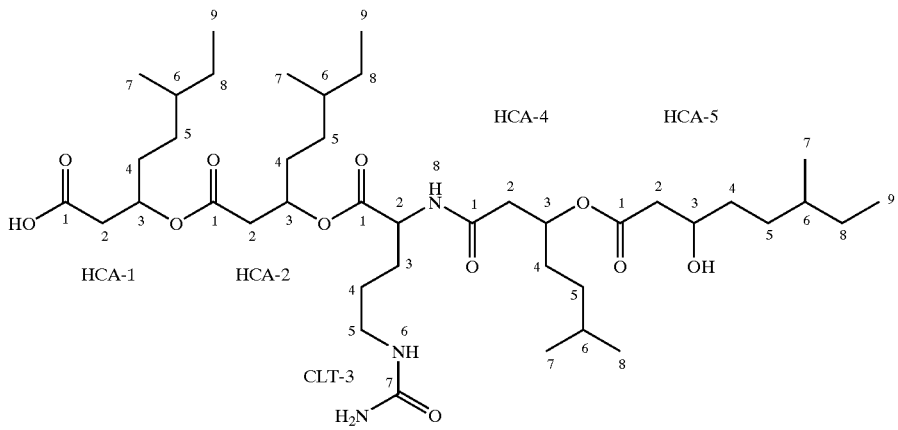

Structure of isomer 1 of Citrullimycine A

Citrullimycine B:

| Retention time: | 7.1 min |
|---|---|
| Molecular formula: | C40H73N3O11 |
| ESI-MS (Electrospray Ionisation Mass Spectrometry): | 770 amu (M-H)⁻ |

MS$^n$ Experiments
ESI⁻:
MS$^2$: 770 amu (M-H)⁻ gave 610 amu (—$C_8H_{16}O_3$), 596 amu (—$C_9H_{18}O_3$), 468 amu, 454 amu, and 440 amu. The products at 610 amu and 596 amu are formed in a 1:1 ratio, the products at 468 amu, 454 amu, and 440 amu are formed in a ratio of 15:58:27.
MS$^3$: 610 amu gave 468 amu (—$C_8H_{14}O_2$), 454 amu (—$C_9H_{16}O_2$), and 440 amu (—$C_{10}H_{18}O_2$). The products are formed in a ratio of 21:62:17.
MS$^3$: 596 amu gave 468 amu (—$C_7H_{12}O_2$), 454 amu (—$C_8H_{14}O_2$), and 440 amu (—$C_9H_{16}O_2$). Ratio: 6:51:43.
MS$^3$: 468 amu gave 425 amu (—HNCO), 330 amu (—$C_9H_{14}O$), 312 amu (—$C_9H_{16}O_2$), and 298 amu (—$C_{10}H_{18}O_2$)
MS$^3$: 454 amu gave 411 amu (—HNCO), 330 amu (—$C_8H_{12}O$), 316 amu (—$C_9H_{14}O$), 312 amu ($C_8H_{14}O_2$), and 298 amu (—$C_9H_{16}O_2$)
MS$^3$: 440 amu gave 397 amu (—HNCO), 316 amu (—$C_8H_{12}O$), 298 amu (—$C_8H_{14}O_2$), and 284 amu (—$C_9H_{16}O_2$)

R1–R4 = 2•Bu, 2•Pr
R1–R4 = 1•Bu, 1•Pent, 1•Et, 1•Pr

Structure of Citrullimycin B (Mixture of Isomers with MW=771 amu)

Citrullimycine C:

| Retention time: | 7.4 min |
|---|---|
| Molecular formula: | C42H77N3O11 |
| ESI-MS (Electrospray Ionisation Mass Spectrometry): | 798 amu (M-H)⁻ |

MS$^n$ Experiments
ESI⁻:
MS$^2$: 798 amu (M-H)⁻ gave 638 amu (—$C_8H_{16}O_3$), 624 amu (—$C_9H_{18}O_3$), and 610 amu (—$C_{10}H_{20}O_3$). The products are formed in the ratio of 5:90:5.
MS$^3$: 624 amu gave 482 amu (—$C_8H_{14}O_2$), 468 amu (—$C_9H_{16}O_2$), 454 amu (—$C_{10}H_{18}O_2$), and 440 amu (—$C_{11}H_{20}O_2$). Ratio: 1.6:96:2:0.4.
MS$^4$: 468 amu gave 425 amu (—HNCO), 330 amu (—$C_9H_{14}O$), 312 amu (—$C_9H_{16}O_2$), 287 amu (—$C_{10}H_{15}O_2N$), and 269 amu (—$C_{10}H_{17}O_3N$)
MS$^5$: 425 amu gave 287 amu (—$C_9H_{14}O$), and 269 amu (—$C_9H_{16}O_2$)
MS$^5$: 312 amu gave 269 amu (—HNCO)
MS$^5$: 269 amu gave 225 amu (—$CO_2$), and 131 amu (—$C_9H_{14}O$)

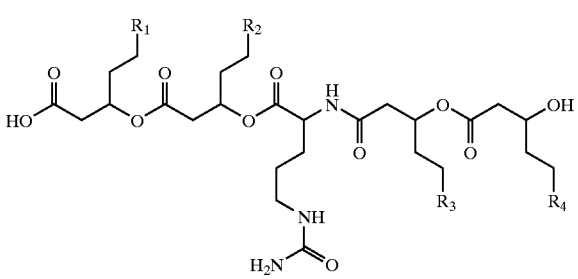

R1–R4 = 4•Bu
R1–R3 = 2•Bu, 1•Pent, R4 = Pr
R1–R3 = 2•Bu, 1•Pr, R4 = Pent

Structure of Citrullimycin C (Mixture of Isomers, MW=799 amu)

TABLE 2

$^1$H and $^{13}$C NMR Spectroscopic Data of Citrullimycine A in MeOD at 300° K.$^a$

|  | $^1$H | $^{13}$C |
|---|---|---|
| HCA1-1$^a$ | — | 171.58$^a$ |
| 2 | 2.59 | 40.30 |
| 3 | 5.18 | 72.21 |
| 4 | 1.62 | 32.90 |
| 5 | b | b |
| 6 | b | b |
| 7 | 0.87 | 19.45 |
| 8 | 1.35/1.15 | 30.51 |
| 9 | 0.87 | 11.73 |
| HCA2-1$^a$ | — | 171.44$^a$ |
| 2 | 2.58 | 40.24 |
| 3 | 5.16 | 72.61 |
| 4 | 1.62 | 32.90 |
| 5 | b | b |
| 6 | b | b |
| 7 | 0.87 | 19.45 |
| 8 | 1.35/1.15 | 30.51 |
| 9 | 0.87 | 11.73 |
| CIT3-1 | — | 175.81 |
| 2 | 4.33 | 53.99 |
| 3 | 1.87/1.68 | 30.25 |
| 4 | 1.55 | 27.73 |
| 5 | 3.12 | −40.6$^a$ |
| 6 | — | — |
| 7 | — | 162.21 |
| HCA4-1 | — | 172.31 |
| 2 | 2.55/2.48 | 41.51 |
| 3 | 5.19 | 73.35 |
| 4 | 1.63 | 32.54 |
| 5 | 1.22 | 35.45 |
| 6 | 1.54 | 29.05 |
| 7 | 0.89 | 23.00 |
| 8 | 0.89 | 23.00 |
| HCA5-1 | — | 172.85 |
| 2 | 2.44 | 43.74 |
| 3 | 3.94 | 69.65 |
| 4 | 1.47 | 35.69 |
| 5 | 1.36 | 33.40 |
| 6 | b | b |
| 7 | 0.87 | 19.45 |

TABLE 2-continued $^1$H and $^{13}$C NMR Spectroscopic Data of Citrullimycine A in MeOD at 300° K.[a]

| | $^1$H | $^{13}$C |
|---|---|---|
| 8 | 1.35/1.15 | 30.51 |
| 9 | 0.87 | 11.73 |

[a]The data of HCA1 and HCA2 are interchangeable.
[b]No assignment possible.

EXAMPLE 4

Bioactivity Assay

SPA [$^3$H] Neurotensin Receptor Binding Assay

Compounds with an affinity for the neurotensin receptor will displace the binding of [3H] neurotensin, which results in a diminished radioactive signal. In the SPA method, receptors immobilized directly on PVT WGA (Wheat Germ Agglutinin) coated SPA beads (Amersham Pharmacia) bind the radiolabelled ligand. The ligand-receptor complex is held in close enough proximity to stimulate emission of light by the bead. Any unbound radioligand is too distant from the bead to transfer energy and therefore will not be detected.

The samples were pre-diluted 1:5 with assay buffer (50 mM Tris-HCl buffer with 1 mM EDTA, 0.2 mM Bacitracin, and 0.1% BSA, pH 7.4) in deep well plates. The final dilution in the assay was 1:20. 96-well isoplates from Wallac were used for the screening. Each well received: 50 μl of sample, 50 μl of membrane in assay buffer (final conc. 16 μg/well), 50 μl of PVT-VGA beads (final conc. 0.75 μg/well), and 50 μl of 4 nM [$^3$H]neurotensin. The plates were sealed and incubated for 2 hours on a shaker (1100 rpm) at room temperature. Prior to counting with a Micro-Beta Trilux (Wallac) the beads were allowed to settle for at least 20 minutes.

On each plate, four wells without samples were used to determine the total receptor-ligand binding and another four wells with 1 μM (L-α, γ-diaminobutyryl) neurotensin were used to determine the nonspecific binding respectively. Inhibition activities are expressed as:
{1-[(dpm sample-dpm nonspecific)/(dpm total binding-dpm nonspec.)]}×100 (%)

The activity of the Citrullimycines was in the range of 16–30 μM. The IC50 of Citrullimycine A was determined to be 16 μM.

We claim:
1. A compound of the formula (I):

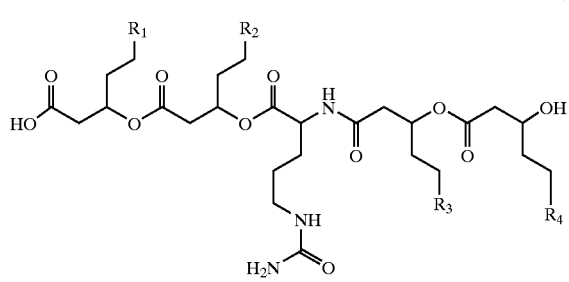

(I)

wherein $R_1$, $R_2$, $R_3$, and $R_4$ are, independently of one another, alkyl residues with 1 to 6 carbon atoms;
or a physiologically tolerated salt thereof,
or an ester, ether, complex, or adduct thereof,
or a stereoisomeric form of:
   a compound of formula (I) as described above,
   or a physiologically tolerated salt of a compound of formula (I) as described above,
   or an ester, ether, complex, or adduct of a compound of formula (I) as described above
or a tautomeric form of:
   a compound of formula (I) as described above,
   or a physiologically tolerated salt of a compound of formula (I) as described above,
   or an ester, ether, complex, or adduct of a compound of formula (I) as described above.

2. The compound of formula (I) as claimed in claim 1, wherein one, two, three, or all of $R_1$ to $R_4$ are butyl residues, and wherein any of the butyl residues may be straight-chain or branched,
or a physiologically tolerated salt thereof,
or an ester, ether, complex, or adduct thereof,
or a stereoisomeric form of:
   the compound of formula (I) as described above in this claim,
   or a physiologically tolerated salt of the compound of formula (I) as described above in this claim,
   or an ester, ether, complex, or adduct of the compound of formula (I) as described above in this claim,
or a tautomeric form of:
   the compound of formula (I) as described above in this claim,
   or a physiologically tolerated salt of the compound of formula (I) as described above in this claim,
   or an ester, ether, complex, or adduct of the compound of formula (I) as described above in this claim.

3. The compound of formula (I) as claimed in claim 1, wherein $R_1$ to $R_4$ are, in any combination, three butyl residues and one propyl residue, and wherein any of the alkyl residues may be straight-chain or branched,
or a physiologically tolerated salt thereof,
or an ester, ether, complex, or adduct thereof,
or a stereoisomeric form of:
   the compound of formula (I) as described above in this claim,
   or a physiologically tolerated salt of the compound of formula (I) as described above in this claim,
   or an ester, ether, complex, or adduct of the compound of formula (I) as described above in this claim,
or a tautomeric form of:
   the compound of formula (I) as described above in this claim,
   or a physiologically tolerated salt of the compound of formula (I) as described above in this claim,
   or an ester, ether, complex, or adduct of the compound of formula (I) as described above in this claim.

4. The compound of formula (I) as claimed in claim 1, wherein $R_1$ to $R_4$ are, in any combination: two butyl and two propyl residues, or one butyl, one pentyl, one ethyl, and one propyl residue, and wherein any of the butyl, propyl, or pentyl residues may be straight-chain or branched,
or a physiologically tolerated salt thereof,
or an ester, ether, complex, or adduct thereof,
or a stereoisomeric form of:
   the compound of formula (I) as described above in this claim,
   or a physiologically tolerated salt of the compound of formula (I) as described above in this claim, or an ester, ether, complex, or adduct of the compound of formula (I) as described above in this claim,
or a tautomeric form of:
the compound of formula (I) as described above in this claim,
or a physiologically tolerated salt of the compound of formula (I) as described above in this claim,
or an ester, ether, complex, or adduct of the compound of formula (I) as described above in this claim.

5. The compound of formula (I) as claimed in claim 1, wherein $R_1$ to $R_1$ are, in any combination: four butyl residues or two butyl, one propyl and one pentyl residue, and wherein any of the alkyl residues may be straight-chain or branched,
or a physiologically tolerated salt thereof,
or an ester, ether, complex, or adduct thereof,
or a stereoisomeric form of:
the compound of formula (I) as described above in this claim,
or a physiologically tolerated salt of the compound of formula (I) as described above in this claim,
or an ester, ether, complex, or adduct of the compound of formula (I) as described above in this claim,
or a tautomeric form of:
the compound of formula (I) as described above in this claim,
or a physiologically tolerated salt of the compound of formula (I) as described above in this claim,
or an ester, ether, complex, or adduct of the compound of formula (I) as described above in this claim.

6. A mixture comprising two or more isomers of a compound of formula (I) as claimed in claim 1.

7. A mixture comprising two or more isomers of a compound of formula (I) as claimed in claim 2.

8. A mixture comprising two or more isomers of a compound of formula (I) as claimed in claim 3.

9. A mixture comprising two or more isomers of a compound of formula (I) as claimed in claim 4.

10. A mixture comprising two or more isomers of a compound of formula (I) as claimed in claim 5.

11. A compound of the formula (I), or a physiologically tolerated salt or an ester, ether, complex, or adduct thereof, or a stereoisomer or a tautomer thereof, as claimed in claim 1, obtainable by cultivation of *Streptomycete* sp. ST 101396 (DSM 13309) or by cultivation of one of the variants or mutants of DSM 13309.

12. A compound of the formula (I), or a physiologically tolerated salt or an ester, ether, complex, or adduct thereof, or a stereoisomer or a tautomer thereof, as claimed in claim 2, obtainable by cultivation of *Streptomycete* sp. ST 101396 (DSM 13309) or by cultivation of one of the variants or mutants of DSM 13309.

13. A compound of the formula (I), or a physiologically tolerated salt or an ester, ether, complex, or adduct thereof, or a stereoisomer or a tautomer thereof, as claimed in claim 3, obtainable by cultivation of *Streptomycete* sp. ST 101396 (DSM 13309) or by cultivation of one of the variants or mutants of DSM 13309.

14. A compound of the formula (I), or a physiologically tolerated salt or an ester, ether, complex, or adduct thereof, or a stereoisomer or a tautomer thereof, as claimed in claim 4, obtainable by cultivation of *Streptomycete* sp. ST 101396 (DSM 13309) or by cultivation of one of the variants or mutants of DSM 13309.

15. A compound of the formula (I), or a physiologically tolerated salt or an ester, ether, complex, or adduct thereof, or a stereoisomer or a tautomer thereof, as claimed in claim 5, obtainable by cultivation of *Streptomycete* sp. ST 101396 (DSM 13309) or by cultivation of one of the variants or mutants of DSM 13309.

16. A process for the production of a compound of formula (I), or a salt or an ester, ether, complex, or adduct thereof, or a stereoisomer or a tautomer thereof, as claimed in claim 1, comprising
cultivating *Streptomycete* sp. ST 101396 (DSM 13309) or one of its variants or mutants,
isolating and purifying one or more target compounds, and
optionally converting said target compound into a physiologically tolerated salt or derivative.

17. The process as claimed in claim 16, wherein the cultivation is carried out at a temperature in the range between about 20°C. and about 35° C. and a pH in the range between about 5 and about 8.

18. A pharmaceutical composition comprising an effective amount of at least one compound of formula (I), or a physiologically tolerated salt or an ester, ether, complex, or adduct thereof, or a stereoisomer or a tautomer thereof, as claimed in claim 1, and a pharmaceutically acceptable carrier.

19. A method for reducing the activity of a neurotensin receptor comprising administering to a patient in need thereof at least one compound of formula (I), or a physiologically tolerated salt or an ester, ether, complex, or adduct thereof, or a stereoisomer or a tautomer thereof, as claimed in claim 1.

20. A method for the production of a pharmaceutical composition, comprising mixing at least one compound of formula (I), or a physiologically tolerated salt or an ester, ether, complex, or adduct thereof, or a stereoisomer or a tautomer thereof, as claimed in claim 1, and suitable excipients and/or carriers, and converting the mixture into a suitable dosage form.

21. Isolated *Streptomycetes* species ST 101396 (DSM 13309).

* * * * *